(12) United States Patent
Gaal et al.

(10) Patent No.: US 11,914,199 B2
(45) Date of Patent: Feb. 27, 2024

(54) OPTICAL FIBER CABLE CONNECTOR

(71) Applicant: IPG Photonics Corporation, Oxford, MA (US)

(72) Inventors: Christopher Gaal, Mansfield, MA (US); Gregory Altshuler, Lincoln, MA (US); Valery Kozlov, Lexington, MA (US)

(73) Assignee: IPG Photonics Corporation, Oxford, MA (US)

( * ) Notice: Subject to any disclaimer, the term of this patent is extended or adjusted under 35 U.S.C. 154(b) by 65 days.

(21) Appl. No.: 17/084,165

(22) Filed: Oct. 29, 2020

(65) Prior Publication Data
US 2021/0157064 A1 May 27, 2021

Related U.S. Application Data

(60) Provisional application No. 63/013,178, filed on Apr. 21, 2020, provisional application No. 62/927,419, filed on Oct. 29, 2019.

(51) Int. Cl.
*G02B 6/38* (2006.01)
*A61N 5/06* (2006.01)
*G02B 6/42* (2006.01)

(52) U.S. Cl.
CPC ............. *G02B 6/3882* (2013.01); *A61N 5/06* (2013.01); *G02B 6/3861* (2013.01);
(Continued)

(58) Field of Classification Search
CPC ............... G02B 6/38; G02B 6/42; A61N 5/06
(Continued)

(56) References Cited

U.S. PATENT DOCUMENTS 3,670,630 A    6/1972   Tyson et al.
4,634,214 A *   1/1987   Cannon, Jr. .......... G02B 6/3865
                                                                          385/86
(Continued)

FOREIGN PATENT DOCUMENTS

AU    2012304605 A1 *   2/2014 ............ A61B 18/22
AU    2014285089 A1 *   2/2016 ........... A61N 5/0601
(Continued)

OTHER PUBLICATIONS

International Search Report of application PCT/US2017/025635, dated Aug. 24, 2017, 2 pages.
(Continued)

*Primary Examiner* — Kaveh C Kianni
(74) *Attorney, Agent, or Firm* — Christensen, Fonder, Dardi & Herbert PLLC; Douglas J. Christensen

(57) ABSTRACT

A laser light energy coupling with a male launch connecter. The male launch connector having a body portion with the fiber optic line terminating at an optical connection component including a male ferrule. The optical connection component being elongate and generally cylindrical with a central circumferential band. The body portion defining a cavity form fit and spaced about the optical connection component. An elastomeric support engaging the optical connection portion provides compliancy when the coupling is made and provides centration before the coupling is made. The elastomeric support positioned rearward of the optical connection component. The elastomeric support may clamp the fiber optic line therein. A forward facing annular surface displaced rearwardly of a forwardmost portion of the male ferrule provides a stop surface when the coupling is made and provides heat transfer means to dissipate heat from the male ferrule through into a receiving coupling.

7 Claims, 13 Drawing Sheets

(52) U.S. Cl.
CPC ......... *G02B 6/3893* (2013.01); *G02B 6/3897* (2013.01); *G02B 6/4206* (2013.01)

(58) Field of Classification Search
USPC ........................................................ 385/78
See application file for complete search history.

(56) References Cited

U.S. PATENT DOCUMENTS

| | | | | |
|---|---|---|---|---|
| 4,747,656 | A * | 5/1988 | Miyahara | G02B 6/3893 385/75 |
| 4,786,135 | A * | 11/1988 | Boero | G02B 6/3888 385/59 |
| 4,991,929 | A | 2/1991 | Bowen et al. | |
| 5,121,454 | A | 6/1992 | Iwano et al. | |
| 5,329,541 | A * | 7/1994 | Brown | G02B 6/4296 385/88 |
| 5,337,386 | A * | 8/1994 | Noll | G02B 6/3893 385/75 |
| 5,574,815 | A | 11/1996 | Kneeland | |
| 5,640,478 | A * | 6/1997 | Roller | G02B 6/3893 385/136 |
| 5,907,650 | A | 5/1999 | Sherman et al. | |
| 5,943,460 | A | 8/1999 | Mead et al. | |
| 6,065,882 | A * | 5/2000 | Roller | G02B 6/4292 385/136 |
| 6,238,103 | B1 * | 5/2001 | Ezawa | G02B 6/3887 385/86 |
| 6,282,349 | B1 * | 8/2001 | Griffin | G02B 6/3813 715/764 |
| 6,394,665 | B1 * | 5/2002 | Hayashi | G02B 6/4292 385/37 |
| 6,432,047 | B1 | 8/2002 | Gust et al. | |
| 6,618,405 | B2 | 9/2003 | Kimura et al. | |
| 6,626,582 | B2 * | 9/2003 | Farrar | G02B 6/3825 385/88 |
| 7,503,701 | B2 | 3/2009 | Hiereth et al. | |
| 7,857,523 | B2 * | 12/2010 | Masuzaki | G02B 6/3891 385/60 |
| 8,366,325 | B2 * | 2/2013 | Ishikawa | G02B 6/421 385/53 |
| 8,419,293 | B2 | 4/2013 | Zerfas et al. | |
| 8,714,836 | B2 | 5/2014 | Daikuhara | |
| 8,888,378 | B2 | 11/2014 | Zerfas et al. | |
| 9,057,847 | B2 | 6/2015 | Lin | |
| 9,329,350 | B2 | 5/2016 | Zerfas et al. | |
| 9,393,081 | B2 * | 7/2016 | Hiereth | A61C 1/0046 |
| 9,395,496 | B2 | 7/2016 | Byer et al. | |
| 9,429,713 | B2 * | 8/2016 | Thornton, Jr. | G02B 6/3866 |
| 9,465,173 | B2 * | 10/2016 | Becker | H01R 13/5219 |
| 9,933,583 | B2 * | 4/2018 | Yan | G02B 6/3825 |
| 10,082,632 | B2 | 9/2018 | Altshuler et al. | |
| 10,663,677 | B2 * | 5/2020 | Altshuler | G02B 6/3893 |
| 2002/0159714 | A1 * | 10/2002 | Lampert | G02B 6/3825 385/60 |
| 2004/0213524 | A1 * | 10/2004 | Foley | G02B 6/4292 385/88 |
| 2005/0067237 | A1 | 3/2005 | Schurmans | |
| 2007/0292087 | A1 * | 12/2007 | Brown | G02B 6/4292 385/92 |
| 2013/0084042 | A1 | 4/2013 | Bouchard et al. | |
| 2015/0301293 | A1 | 10/2015 | Seetharam et al. | |
| 2015/0374207 | A1 * | 12/2015 | Fukuoka | G02B 23/2446 600/110 |
| 2017/0285276 | A1 * | 10/2017 | Altshuler | G02B 6/3624 |
| 2018/0164510 | A1 | 6/2018 | Shouda | |
| 2019/0094472 | A1 | 3/2019 | Altshuler et al. | |
| 2021/0048586 | A1 | 2/2021 | Altshuler et al. | |

FOREIGN PATENT DOCUMENTS

| | | | | |
|---|---|---|---|---|
| CA | | 2613074 A1 * | 1/2007 | ............ A61B 18/22 |
| DE | | 4201769 C1 | 4/1993 | |
| EP | | 0992343 A1 | 4/2000 | |
| JP | | 59-147110 U | 10/1984 | |
| JP | | 63-164711 U | 10/1988 | |
| JP | | 01-176803 U | 12/1989 | |
| JP | | 03-293304 A | 12/1991 | |
| JP | | 04-090635 A | 3/1992 | |
| JP | | 2012194410 A | 10/2012 | |
| WO | WO2004/097986 A2 | | 11/2004 | |
| WO | WO2005/119319 A2 | | 12/2005 | |
| WO | WO2010/124165 A1 | | 10/2010 | |
| WO | WO2013/126429 A2 | | 8/2013 | |
| WO | WO2014/151927 A1 | | 9/2014 | |
| WO | WO 2017/173419 A1 | | 10/2017 | |

OTHER PUBLICATIONS

International Search Report of application PCT/US2020/057978, dated Feb. 18, 2021 (2 pages).
Japanese Office Action from a corresponding Japanese Application No. 2022-011829 with an English translation; dated Nov. 28, 2022; 10 pages.
Final Office Action from corresponding U.S. Appl. No. 17/724,343 dated Sep. 19, 2023—9 pages.
Supplementary European Search Report and the European Search Opinion from corresponding European Patent Application No. 20882698.2 dated Sep. 15, 2023—8 pages.

* cited by examiner

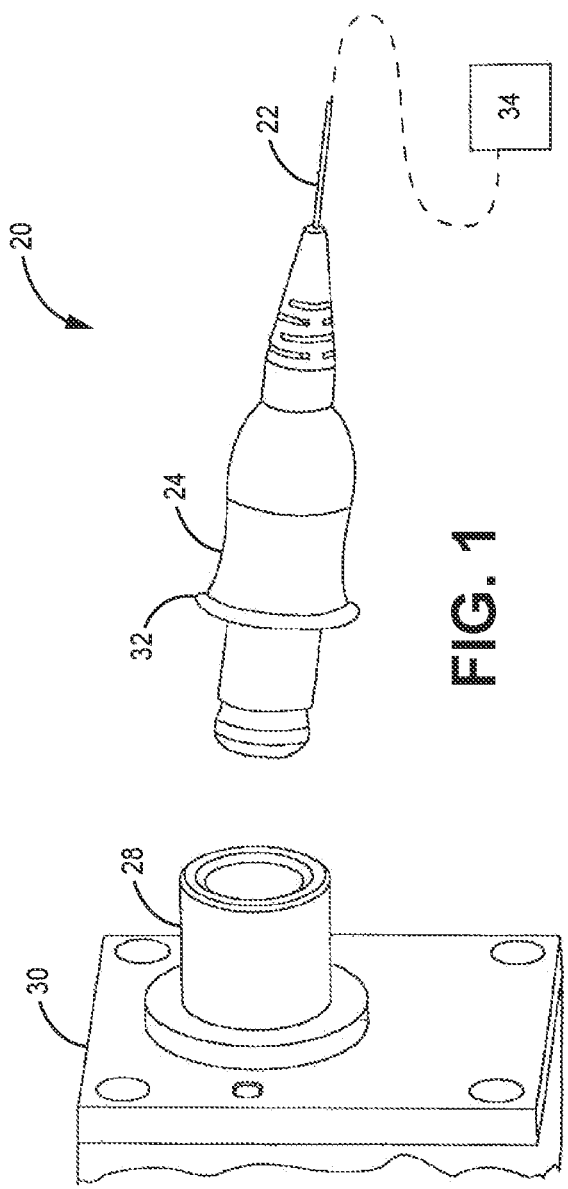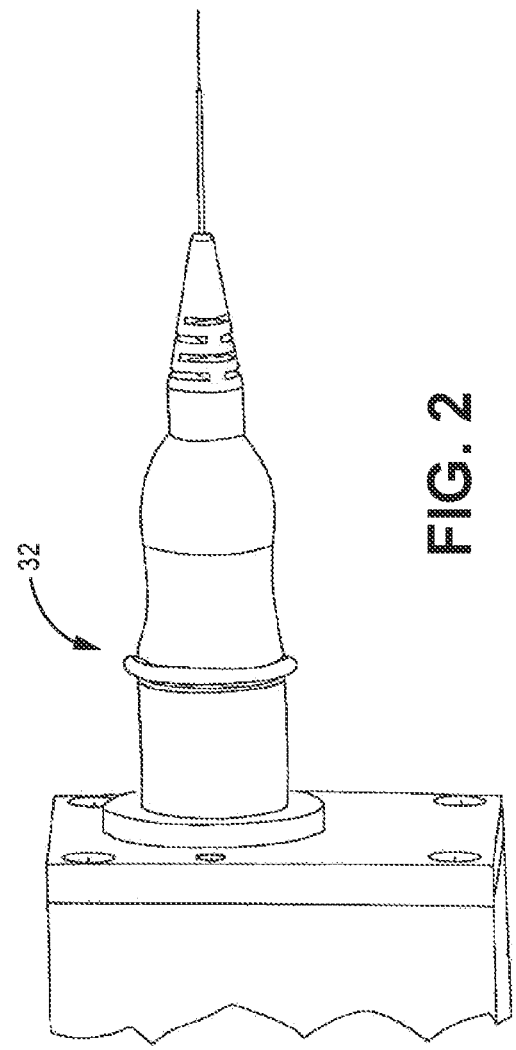

OPTICAL FIBER CABLE CONNECTOR

This application claims priority to U.S. Provisional Application No. 63/013,178 filed on Apr. 21, 2020, and U.S. Provisional Application No. 62/927,419 filed Oct. 29, 2019. Both applications are incorporated by reference herein.

This application is related to U.S. Pat. Nos. 10,082,632 and 10,663,677, owned by the owner of the instant application. These patents are incorporated by reference herein for all purposes.

BACKGROUND OF THE INVENTION

Laser-based medical devices use laser radiation for medical treatments. The laser radiation type, power, and parameters vary depending upon the treatment. A laser energy generator connects to a medical device using connection systems having an optical connection portions and a mechanical connection portions.

The connector is a critical component of the delivery system. Generally the size of optical fiber connectors have decreased over time due to the desirability of a higher density of connectors on telecommunications equipment; that is, more connectors per square inch of equipment space. Typical connectors for medical purposes comprise slightly modified optical connectors developed for telecommunication devices use, such as SMA-905 or SMA-906 modified connectors with a forward projecting ferrule with an exposed fiber facet. Such connectors are of small size and the mating components are also small, specifically, the ferrule securing the optical fiber and the cooperating female component. The small size of the graspable portion requires delicate manipulations to make the optical fiber connection to the medical device. The small sized connectors are not conducive to handling with gloves, nor making a quick connection. Also, it is easy to contaminate or damage the input fiber facet during mating with a medical device connector on the laser energy generator as the facet is exposed and defines the furthermost portion of the connector. Any issue associated with the integrity of the connection between the laser source and medical device can impact the performance of the medical device and potentially the medical procedure.

In medical laser applications compared to telecommunications, the fiber and connection needs to efficiently pass much higher power levels. Where there is a miniscule misalignment of the optical connection portions, there can be excessive heat generation in the connection and power loss to the medical device. The excessive heat generation can damage the connector portions, particularly where there is insufficient heat management means associated with the connector portions.

Most conventional fiber optic connectors for laser applications have the optical connection portions essentially fixed within the mechanical connection portions. In telecommunications applications, where alignment of the optical connection portions is not critical, this fixed relationship between the optical connection portion and the mechanical connection portion is satisfactory. This is in part due to the low power handling requirements of such telecommunications connectors. Heat management is not a significant factor and slight misalignments is not a significant issue. Optic fiber connectors in laser telecommunications applications are commonly connecting one optic fiber to another optic fiber and such connections have one optic fiber face confronting another optic fiber face. Thus, adequate alignment between optical connection portions of cooperating connectors is relatively simple and having the optical connection portions fixed to the mechanical connection portions is not a significant issue.

This compares to launch connectors in laser medical devices where there is a high criticality associated with alignment and in some cases heat management. In typical laser energy generators for medical devices, the launch connector that connects with the laser energy generator has an internal exposed fiber optic face that must be aligned with a conical focused laser beam at the connection of the laser generator. Any misalignment can cause energy losses and excessive heating of the connector portions.

Significant strides have been made in launch connectors for medical devices that plug into laser energy generators. Separating and isolating the mechanical connection portions from the optical connection portions and allowing the optical connection portion of the launch connector, for example a cylindrical male ferrule with the optical fiber face at a forward end, to resiliently float within the annular mechanical portion of the launch connector can provide acceptable alignment when mated with a female ferrule with a cylindrical bore at the laser generator. See U.S. Pat. No. 10,663,677 to the owner of the instant application. Said application is incorporated by reference herein for all purposes. The '677 patent discloses embodiments where the cylindrical male ferrule is supported within a uniform diameter bore of the housing exclusively by the fiber optic cable. Other embodiments disclose the cylindrical male ferrule is supported within a uniform diameter bore of the launch connector housing with elastomeric material positioned rearwardly of the male ferrule providing centration of the male ferrule. Although these embodiments offer improvements over known launch connectors for medical applications, any further improvements relating to easier manufacturing, assembly, robustness, and heat management would be well received.

SUMMARY

A delivery system extending from a laser radiation source for connecting to a medical device that utilizes the laser radiation for medical treatment. The delivery system comprises an optical cable with an optical fiber extending from the laser source with a male launch connecter having a male ferrule on the optical cable. The launch connector couples to a receiving connector having a female ferrule that interfaces with the male ferrule on the medical device. The male launch connector having a body portion with an outer wall defining an interior and with a tubular portion projecting forward with an outermost or forwardmost edge and having a central axial recess defined therein. The optical fiber terminating at the male ferrule positioned in the central recess rearward of the forwardmost edge of the body portion and presenting a forward facing fiber facet. In embodiments, when not connected to the receiving connector, the male ferrule is compliantly positioned within the central recess. In embodiments, when the launch connector is not connected, the male ferrule is compliantly positioned by way of an elastomeric material directly or indirectly supporting the male ferrule with respect to the body portion and with circumferentially and axially extending conforming spacing between the male ferrule and wall surface of the body portion in the central axial recess providing a defined freedom of movement in all radial directions and axial compliancy of the male ferrule.

In embodiments, the male ferrule is seated in a rigid sleeve with the ferrule extending forwardly from the sleeve, the sleeve engaging and/or supported by an elastomeric material that is seated in the body portion, the sleeve spaced from the interior body wall surface providing the radial compliancy and resiliency in all radial directions when the launch connector is not attached to the receiving connector. In embodiments, compliancy and resiliency is provided in forward and rearward axial directions. In embodiments, the elastomeric material is configured as an annular member extending between the sleeve and interior wall surface of the body portion. In embodiments, the elastomeric material is configured as one or more blocks of elastomeric material with a rearward edge or edge portion of the rigid sleeve engaging or confronting the elastomeric material.

I

In embodiments, the male ferrule, any sleeve or fitting thereon, and the optical fiber and any coverings thereon are supported within the body portion, when not connected to a receiving connector, exclusively by way of compliant material providing centration and compliancy. In embodiments, the compliancy is in all directions. In embodiments, movement of the ferrule is constrained by the body portion or other structure of the launch connector that encompasses the male ferrule and any sleeve or fitting thereon. The body portion or other structure can provide a form fitting cavity for the male ferrule and any sleeve or fitting thereon.

In embodiments the components of the launch connector assembly together with minimal or no welding, glues, adhesives, or separate fasteners. In embodiments, all exteriorly facing components, the forward plug portion, the handle portion, and the strain relief member are assemblable without welding, glues, adhesives, or separate fasteners, and are retained together by polymer features on the components.

In embodiments, clam shell halves of a body portion that define the handle portion and a portion of the launch connector housing, are retained by snap together features on the polymer clam shell halves, and the optical connection portions and the plug are retained in the housing by conforming features molded into the polymer clam shell halves. In embodiments, a housing of the launch connector comprises a polymer handle portion molded as a single unitary component and a polymer forward plug portion molded as a single unitary component. The launch connector is rotatingly assembled by way of cooperating threaded connection portions, one unitary with the handle portion and one unitary with the forward plug portion. Upon assembly, the threaded connections are concealed. In embodiments, an O-ring is in the juncture between the plug portion and the handle portion, with the O-ring being compressed as the connection is made providing exterior pressure on the respective plug portion and handle portions of the housing, resisting any disconnection torques and providing a hermetic seal. In embodiments, the O-ring is compressed at an angle to the axis of the plug portion, the measurement of the acute angle of the respective axis is greater than 20 degrees and less than 70 degrees. In embodiments, the polymer plug portion and the polymer handle portion of the housing may be snap-fit assembled by pushing them together axially where cooperating features on connection portions of the components mate.

In embodiments, a launch connector has a polymer housing defined by a nose or plug portion and a grasping or handle portion, the plug portion defining a mechanical connection portion of the launch connector. An optical connection portion has a compliantly centrated rigid male ferrule component connected to the optical fiber and compliantly centrated by a support formed of elastomeric material that is positioned rearwardly of and that is engaging and/or capturing the rearwardmost portion of the rigid male ferrule component. In embodiments, none of the rigid male ferrule portion of the optical connection portion extends rearwardly of the elastomeric support. In embodiments, the compliantly centrated male ferrule component extends forwardly from the elastomeric support and is cantilevered therefrom. In embodiments, the elastomeric support is a cup shaped member with a central opening for the optical fiber. In embodiments, the elastomeric support is block shaped with two separable portions that grasp or clamp onto the optical fiber that extends therethrough. In embodiments, when the launch connector is connected to the laser energy generator at the female coupling portion, the elastomeric support is primarily deflected axially and thereby primarily compressed.

In embodiments, tension on the optical fiber and any coverings thereon may provide a compressive condition of the sleeve with elastomeric material when the launch connector is not connected to the receiving connector.

In embodiments, the optical fiber and any coverings thereon are compliantly and resiliently connected to the body portion by way of elastomeric material that also engages and supports the male ferrule portion of the optical connection portion.

In embodiments, the optical cable has sheathing that is engaged with a rearward end of the body portion at spaced discrete attachment regions.

In embodiments, the male ferrule having freedom of movement provided by the flexibility of the optical cable forward of the anchor position. The ferrule may be constrained laterally by structure within or part of the body portion such as a tubular portion of the body portion thereby limiting the lateral freedom of movement. Such structure providing a circumferential gap around the ferrule for the entire length of the ferrule when the ferrule is axially centered within the tubular portion. In embodiments a resilient material may be attached to the rearward end portion of the male ferrule for controlling the radial or lateral freedom of movement that does provide some resistance to lateral movement beyond that provided by the optical fiber or cable.

In embodiments, the male ferrule having freedom of movement provided by the flexibility of the optical cable forward of the anchor position and the engagement of the rearward portion of the optical connection portion with an elastomeric member. In embodiments the optical connection portion may be a ferrule or a ferrule seated in a sleeve. The ferrule may also be constrained laterally and axially by structure within or part of the body portion such as a tubular portion of the body portion thereby limiting the lateral freedom of movement of the optical connection portion. Such structure providing a circumferential gap around the ferrule for the entire length of the ferrule when the ferrule is axially centered within the tubular portion. In embodiments a resilient material may be attached to the rearward end portion of the male ferrule for controlling the radial or lateral freedom of movement that does provide some resistance to lateral movement beyond that provided by the optical fiber or cable.

In embodiments, the ferrule having registration surfaces such as an outer cylindrical surface that registers with a cooperating inwardly facing cylindrical surface on the female ferrule of the receiving connector without the female ferrule having an axial stop for the male ferrule in the optical registration receiver. The male ferrule being slidingly received within an inwardly facing cylindrical surface of the female ferrule with the only contact of the cooperating ferrules being between the respective cylindrical surfaces. The inventors having discovered that focused laser energy at the forward face of the male ferrule, in particular at the fiber facet, can generate substantial excess heat that is advantageously managed. The interfaces of the respective cylindrical surfaces of the male and female ferrule may not be adequate for managing and providing adequate heat transfer away from the male ferrule. The inventors have further discovered that heat dissipation of the focused laser energy on the front face of the male ferrule is preferably managed by transferring and dissipating heat through the medical device connector on the laser energy generator as such provides heat sink capabilities way greater than that of the launch connector and attached fiber optic cable. The receiving connector and associated structure is more suitable for dissipating excess heat that is the launch connector and fiber cable to the medical device. The inventors have discovered that axially confronting surfaces, particularly surfaces urged together under compression, transfer heat from the launch connector to the receiving connector more efficiently than the sliding cylindrical surfaces of a male ferrule and female ferrule.

A feature and advantage of embodiments is a launch connector with a male ferrule that engages a receiving connector on a laser energy generator by way of a sliding engagement of an exterior cylindrical surface of the male ferrule with an inwardly facing cylindrical surface of a female ferrule. Laser energy focused on the front side of the male ferrule thereby heating the male ferrule. A tubular sleeve encompasses the male ferrule and has a forward facing annular leading surface that is perpendicular to the connector axis, that engages a cooperating annular surface on the receiving connector. In embodiments the cooperating annular surface is an annular surface of the female ferrule. In embodiments, the forward facing annular surface of the sleeve supporting the male ferrule is compressively engaged with the cooperating annular surface of the female ferrule by way of compression of a resilient portion rearward of the front face of the male ferrule. In embodiments the resilient portion is an elastomeric material positioned between the tubular sleeve and the body of the launch connector. In embodiments, the elastomeric material is configured an annular member. In embodiments the elastomeric material is a block or blocks that engage a rearward end of the tubular sleeve.

In embodiments, a launch connector connects to a receiving connector on a laser energy generator with a heat transfer pathway extending from the male ferrule through an annular heat transfer member that is interior to a gripping portion of the launch connector and that engages with a annular engagement member of the receiving connector, the laser energy generator providing a heat sink for the heat energy transferred from the male ferrule. In embodiments, a resilient member provides rearward axial displacement of the annular heat transfer member and provides a forward bias to provide a compressive engagement with the annular engagement member of the receiving connector when connected.

Conventional optical fiber connector art rely upon axial stop surfaces that engage the forward face of the male ferrule. In the context of a launch connector this complicates the male ferrule to female ferrule engagement. In embodiments, the forwardmost front end of the male ferrule does not engage any stop surfaces. A shoulder rearwardly of the forwardmost front end may engage an annular surface of the female ferrule when the connection is made. The shoulder-annular surface engagement providing a path of heat dissipation generated by the laser beam energy focused on the forward facet of the optic fiber in the male ferrule.

In embodiments of the invention, the optical fiber rearwardly of the ferrule is fixed to an elastomeric support member providing axial cushioning and or resilience when the ferrule engages with a portion of the connector of the medical device. The fixation of the optical fiber with respect to the launch connector body may be in resilient elastomeric disks defining diaphragms.

In embodiments of the invention, the ferrule is slidingly received in a bore of an optical registration receiver, the optical registration receiver may have a tapered concave lead-in registration surface and a cylindrical registration surface, the male ferrule having a cooperating convex outer tapered surface and a cylindrical registration surface to closely engage the cylindrical registration surface of the optical registration receiver.

In embodiments of the invention, the outer tubular portion of the launch connector engages with a mechanical registration receiver of the receiving coupling attached to, for example, a laser energy generator. The leading edge of the tubular outer portion and/or the outermost edge of the mechanical registration receiver may be tapered to provide an insertion tolerance.

A feature and advantage of embodiments of the invention is an optical fiber launch connector with a single fiber that has an internal movable ferrule positionally fixed only by way of a single optical fiber, any sheaths on the fiber, and an elastomeric material. The ferrule positionally constrained by but not positionally fixed by being partially positioned in the bore of an inner tubular portion of the launch connector. A feature an advantage of embodiments is that no metal springs and no coil springs are utilized in positioning the male ferrule in the launch connector and the resiliency and compliancy with respect to the positioning of the male ferrule (and any sleeve thereon) is provided by elastomeric material and/or the fiber optic cable (and any sheathings thereon). In such embodiments, the compliancy of the male ferrule in the launch connector is believed to be more readily controlled, the assembly and manufacturing is believed to be easier, the complexity of the componentry is less, all due to utilizing elastomeric material rather than metal springs and/or coil springs.

In embodiments, the launch connector is assembled by: having one of the two clam shell halves of the housing open with one part of the elastomeric material positioned in the one of the two clam shell halves positioned rearwardly of a receiving region of the male ferrule or male ferrule and sleeve combination; laying a male ferrule or male ferrule and sleeve combination into the one of the two clam shell halves, with the fiber optic (and any sheathings thereon) extending from the male ferrule or male ferrule and sleeve combination laying on a surface of the one part of the elastomeric material, and with the rearward end positioned at a forward surface of the one part of the elastomeric material and with the male ferrule or male ferrule and sleeve combination lawing in a defined cavity for receiving the male ferrule or male ferrule and sleeve combination; and closing onto the one of the two clam shell halves the other of the two clam shell halves and securing the two clam shell halves together. The other may have a second part of the elastomeric material thereby pinching or otherwise securing or constraining the fiber optic and any sheathings thereon between the first and second parts of the elastomeric material when the two clam shell halves are assembled together. In embodiments, the two parts of the elastomeric material may define two webbings at the forward facing portion of the elastomeric material, the two webbings supporting the fiber optic and any sheathings thereon.

A feature and advantage of embodiments of the invention is an optical fiber launch connector with a single fiber that has an internal movable ferrule fixed only to the single optical fiber and optionally to sheaths on the fiber. The ferrule positionally constrained by but not positionally fixed by being partially positioned in the bore of an inner tubular portion of the launch connector.

A feature and advantage of embodiments of the invention is a optical fiber coupling with cooperating connectors, one connector being a launch connector with a ferrule supporting an optical fiber with a fiber facet, the other connector receiving the one connector and having an optical registration receiver that receives the ferrule. Each connector having the optical connecting portion of the connector recessed from the exterior of the connector.

In embodiments, an optical connection portion including a ferrule is retained in a launch connector housing by way of an optical fiber extending rearwardly from the optical connection portion, the optical fiber being clamped by an elastomeric block rearward of the optical connection portion, a rearward end of the optical connection portion confronting a forward facing surface of the elastomeric block. In embodiments, the optical fiber is under tension and the elastomeric block is compressively loaded by the rearward end of the optical connection portion. In embodiments, the optical connection portion comprises a glass or ceramic ferrule seated in a metal sleeve, the metal sleeve providing a circular rearward engagement end that engages and compresses the elastomeric sleeve. In embodiments, the optical connection portion comprises a stainless steel ferrule. In embodiments, the clamping of the fiber optic in the elastomeric block allows axial compliancy of the fiber optic and axial compliance of the optical connection portion. In embodiments, the fiber optic extends centrally through the elastomeric block, the elastomeric block formed of two separable block portions. The fiber optic sandwiched between the two separable block portions with an interference fit between the fiber optic and the block portions.

In embodiments, the optical connection portion of the launch connector having a forward cylindrical portion, a mid cylindrical portion diametrically larger than the forward cylindrical portion, and a rearward cylindrical portion diametrically smaller than the mid cylindrical portion. The forward cylindrical portion having a central axial bore sized to the fiber optic and the fiber optic secured therein and having an end exposed at the front end of the forward fiber optic. In embodiments the forward cylindrical portion is diametrically equal to the rearward cylindrical portion. In embodiments, the housing of the launch connector provides an interior cavity conformingly shaped to the three cylindrical portions of the optical connection portion of the launch connector. In embodiments, the three cylindrical portions are provided by a glass or ceramic cylindrical ferrule extending from a stainless steel fitting, the stainless steel fitting providing the cylindrical mid portion and the cylindrical rearward portion and the glass or ceramic cylindrical ferrule providing the forward cylindrical portion. In embodiments, the three cylindrical portions are provided by a unitary stainless steel ferrule. In embodiments the ferrule may be of other compositions, for example ceramic material.

In embodiments, a cooperating pair of connectors for connecting a laser source to a medical device for delivery of laser energy, each connector having an outer mechanical coupling portion and an inner optical coupling portion, each of the outer mechanical coupling portions configured as an outer tubular portion with a forward edge, each outer tubular portion having a tubular wall and defining respective axial recesses, the optical coupling portions concentrically positioned within the axial recesses and spaced from the tubular walls, the optical coupling portions inset from the respective forward edges. In embodiments, one connector provides an optical cable with an optical fiber connecting to a ferrule and presenting a fiber facet. The ferrule having a central position, the ferrule received within a female portion of an optical registration receiver. In embodiments, one of the tubular mechanical coupling portions interlaced between the tubular mechanical coupling portion of the other coupling and the optical coupling portion of the other coupling. The tubular mechanical coupling portions slidingly engaged with one another. In embodiments, the connector supplying the laser energy to the medical device, a launch connector, has its outer tubular portion extending within the outer tubular portion of the connector associated with the medical device. In embodiments, as the connectors are manually manipulated, the outer mechanical couplings engage first and bring the connectors into an axial alignment as the outer mechanical couplings are slidingly engaged and brought together, the connectors become axially aligned before the optical coupling portions engage each other. The optical coupling portions then are prealigned and as the optical coupling portions engage with tapered surfaces on one or both optical coupling portion, the optical couplings are brought into final operational alignment. In embodiments one optical coupling portion is laterally movable with respect to its respective mechanical coupling portion.

DESCRIPTION OF THE FIGURES

FIG. 1 is a perspective view of a delivery system with a launch connector disconnected from a connector on a laser energy generator in accord with inventions herein.

FIG. 2 is a perspective view of launch connector of FIG. 1 connected to the laser energy generator.

DETAILED DESCRIPTION

Figure 3:
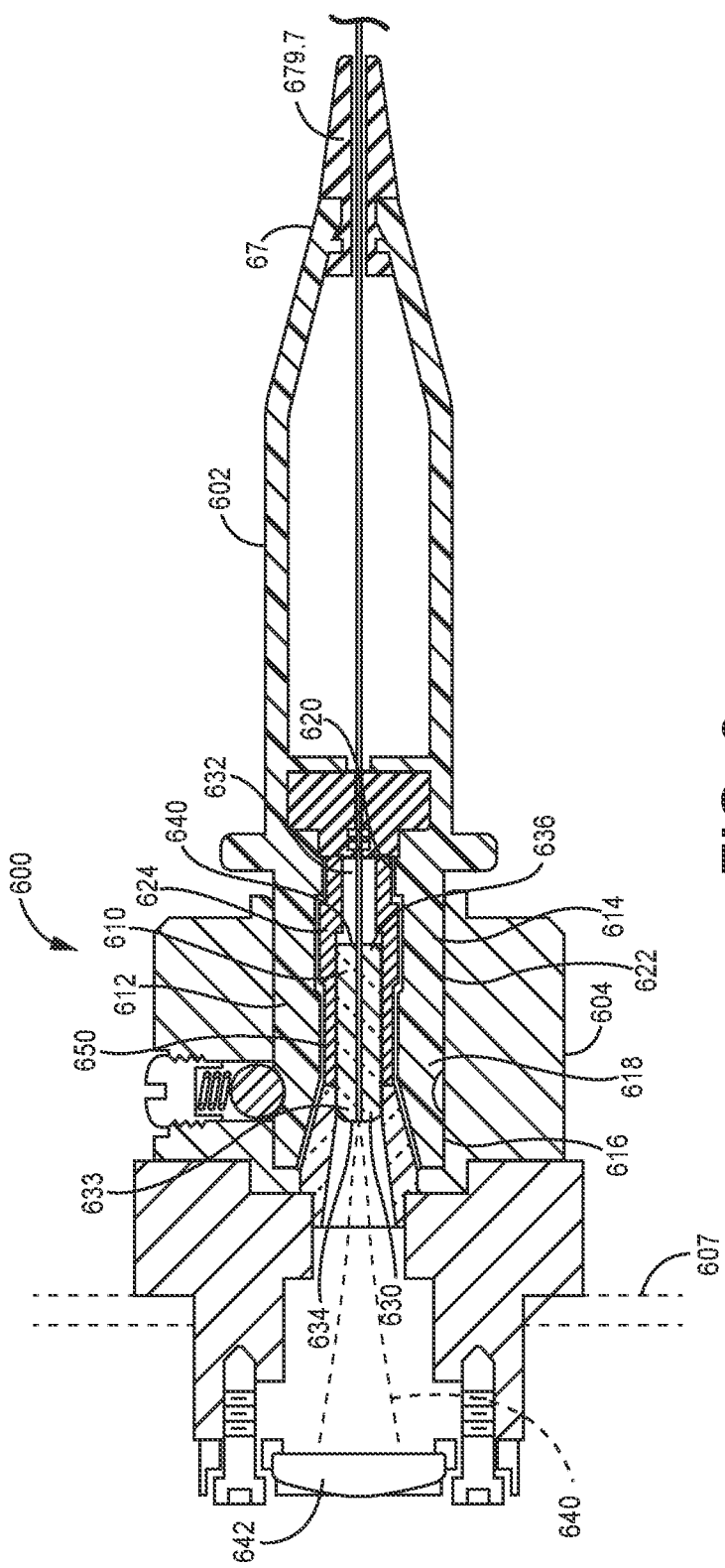
FIG. 3 is a cross sectional view of a coupling including a launch connector and a receiving connector according to embodiments.

Referring to FIGS. 1 and 2, a laser energy delivery system 20 comprises a optical fiber cable 22 and a launch connector 24. The launch connector 24 and a connector 28 defining an optical fiber coupling 32 for providing laser radiation to the medical device 34 from the laser radiation source 30.

Figure 11:
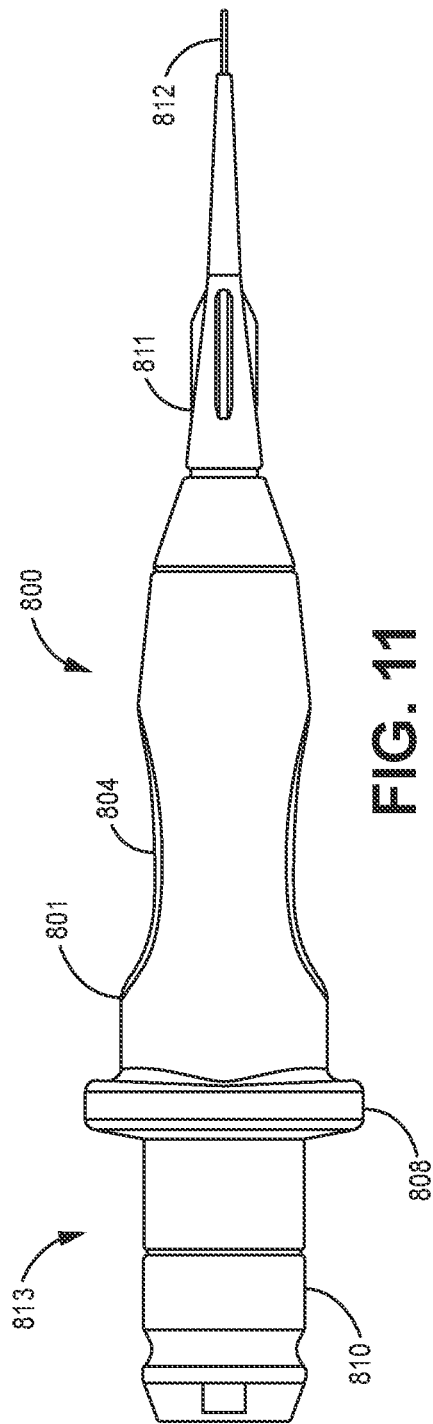
FIG. 11 is a perspective view of another launch connector in accord with embodiments.

Referring to FIGS. 3, 4, 5 and 6, a coupling 600 comprises a launch connector 602 and a medical device connector 604 that receives the launch connector, the medical device connector receiving the launch connector and being part of a laser energy generator 607. The launch connector comprising an optical connection portion 610 and a mechanical connection portion 612. The mechanical connection portion of the launch connector comprising a body portion 614 with a forward projecting tubular portion 616 having a tubular wall portion 618 with an interior wall surface 620, an exterior wall surface 622, and a forward annular stop surface 623. The optical connection portion comprising an optical connection component 624 with a male ferrule 630 and a fiber optic line 632 extending therefrom. The male ferrule having a forward portion 633, a forward face 634, a rearward portion 636, a cylindrical surface 638, and a rear end 640 from which the fiber optic line 632 extends. A fiber facet 642 is exposed at the front face of the male ferrule. The optical connection component 624 may further comprise a rigid fitting 650 configured as a sleeve within which the male ferrule 630 is fixed. The sleeve may be formed of a highly heat conductive material such as stainless steel, other materials and metals may also be suitable. The sleeve having a forward edge 656, a forward tubular portion 658, a mid tubular portion 660, and a rearward tubular portion 662. The mid tubular portion having a larger diameter than the forward and rearward tubular portions and include forward and rearward stop surfaces 670, 672 that confront respective forward and rearward stop surfaces 674, 676 on the tubular wall portion 618. The body portion 614 defines a cavity 677 that conforms to the male ferrule 630 and attached sleeve 650, providing a limited amount of freedom of motion of the ferrule and sleeve. The sleeve may be engaged and supported by elastomeric material 678 configured as a block 679. The block can have respective block parts 679.1 which may be configured as halves as shown in FIG. 11 for attachment about the fiber optic line. The block parts 679.1 may further have cavities 679.3 which provided webbings 679.5 at the forward end of the elastomeric material 678. The fiber optic line may be further anchored at the tail 679.6 of the body portion such as by an elongate grommet 679.7 configured as a strain relief member.

The receiving connector 604, comprises an optical connection portion 680 and a mechanical connection portion 682. The optical connection portion having a female ferrule 683 with an inwardly facing cylindrical surface 684 that cooperates with the outer cylindrical surface 638 of the male ferrule. The laser energy generator 607 providing a focused energy beam 640 from the lens 642 on the fiber facet 642 of the male ferrule.

The mechanical connection portion receiving the forward projecting tubular portion 616, or nose portion, of the launch connector in recess 686 defined by laser energy generator connector housing 687.

Heat generated from the focused energy beam on the male ferrule may be dissipated by way of a heat path 690 illustrated by the arrows that extends from the male ferrule to the sleeve to the outward annular face 692 of the female ferrule 683 to the housing 695 or other structure of the laser energy generator 607. The housing 687 or other structure of the laser energy generator connector acts as a significant heat sink for dissipating the heat from the male ferrule. The heat capacity, that is the capability of the sleeve, particularly when formed of metal such as steel, is substantially greater than polymers such as may be used for the body portion of the launch connector.

When the connection is made and the sleeve pushes rearward against the elastomeric member, the resiliency of the elastomeric member can provide a compressive force of the forward annular face of the sleeve on the outward annular face of the female ferrule. The compressive force assists in an enhanced thermal connection between the respective components. In other embodiments, the heat flow path may be through other structures other than the female ferrule.

Referring to FIGS. 7-10, in embodiments, a launch connector 700 has a housing 701 configured as a body portion 702 with a grasping portion 704, a tail portion 706, a forward flange 708, and a nose portion 710 that projects forward from the grasping portion 704 for insertion into the receiving connector of a laser radiation source as described previously. An optical connection portion comprising a male ferrule 711 is compliantly positioned within the body portion at the nose portion. In other embodiments, a cylindrical male ferrule may be seated in a fitting as previously illustrated.

Figure 8:
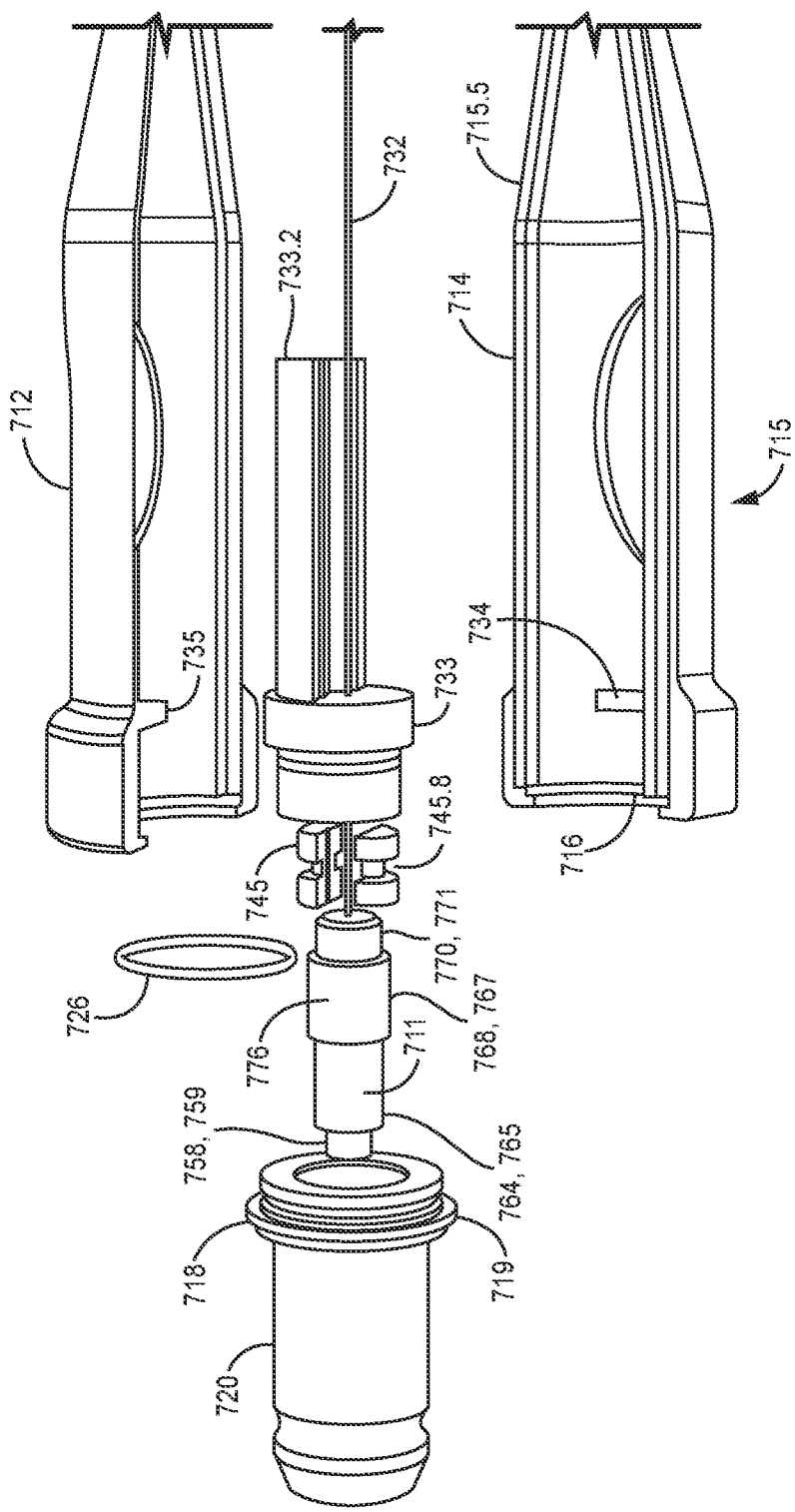
FIG. 8 is an exploded view of the launch connector of FIG. 7.
Figure 9:
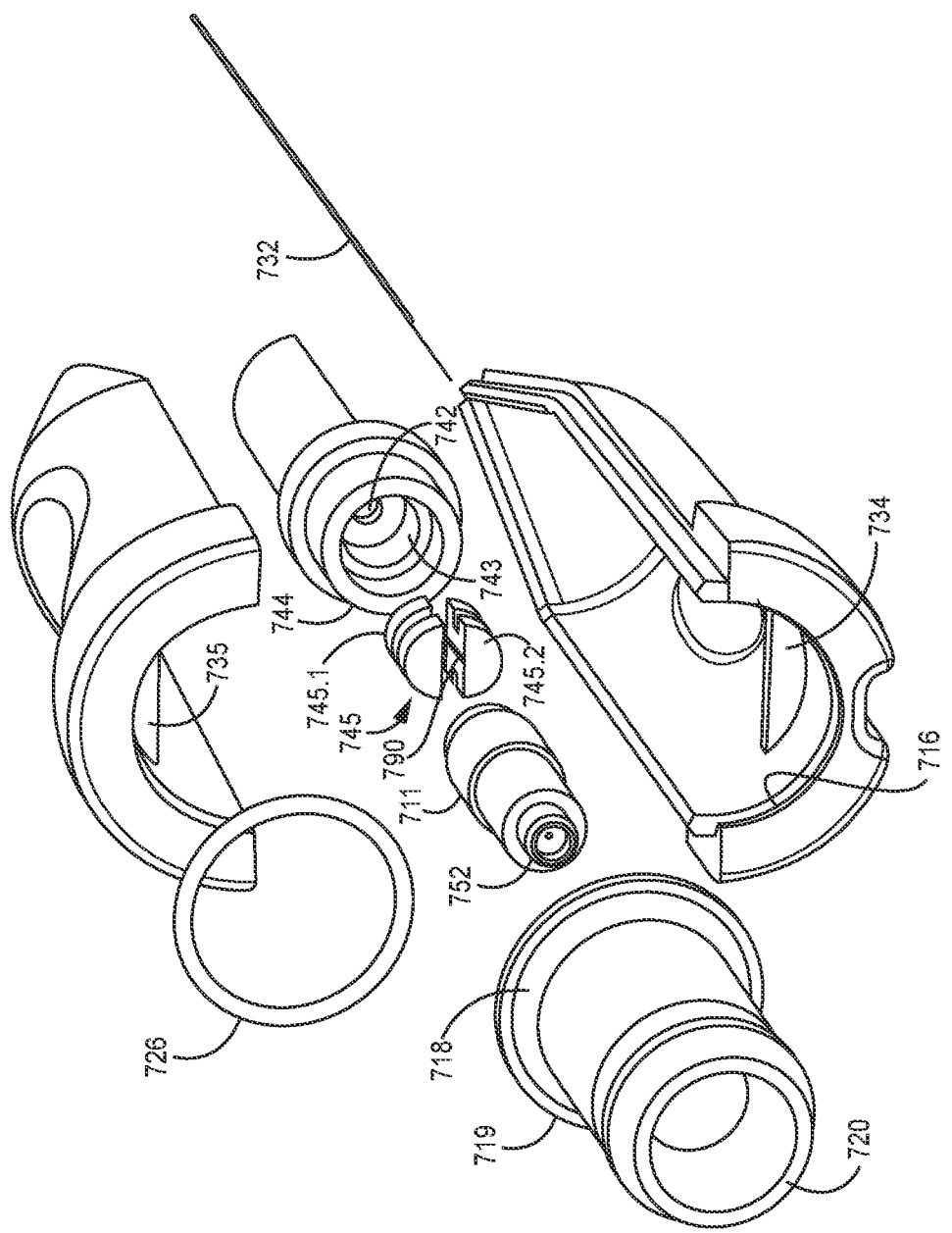
FIG. 9 is another exploded view of the launch connector of FIG. 7.
Figure 10:
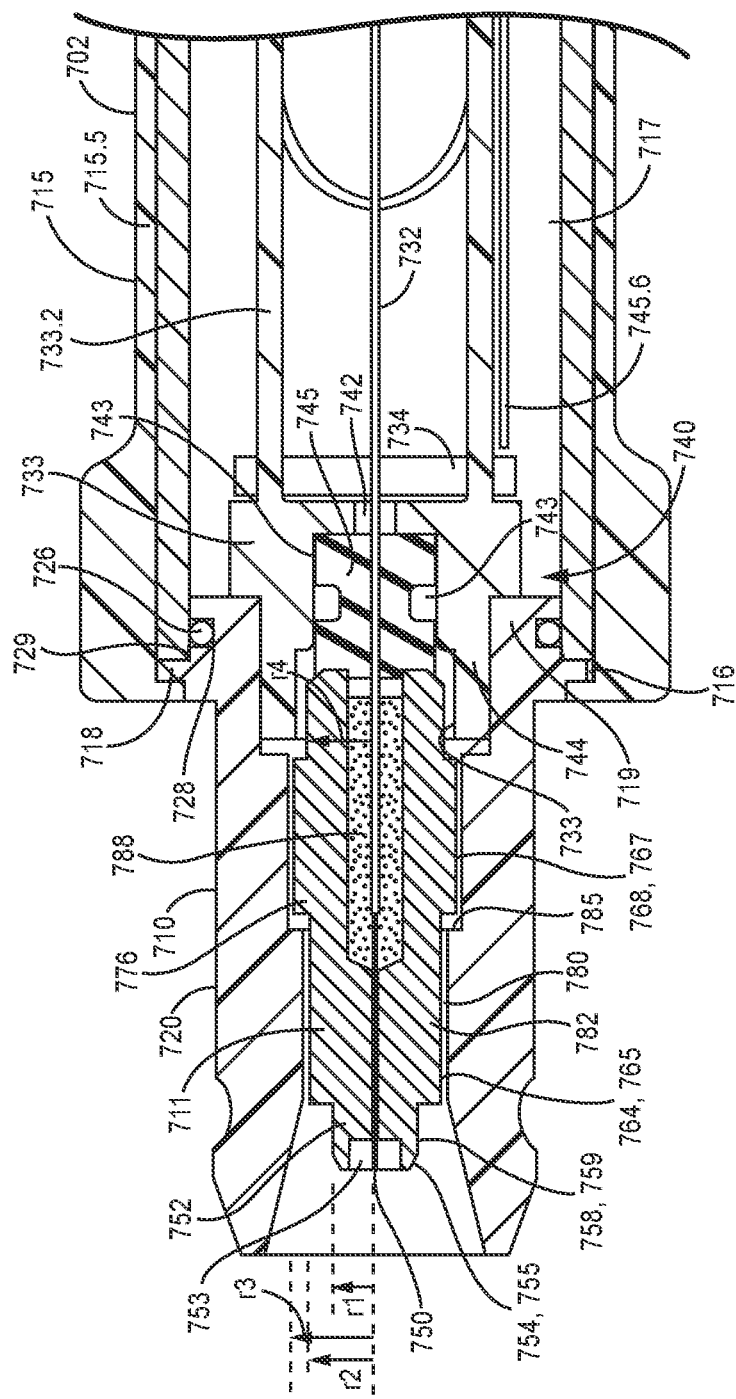
FIG. 10 is a cross-sectional view of the launch connector of FIG. 7.

As best illustrated in FIGS. 8-10, the body portion, in embodiments, may comprise three exterior components and an interior component. Specifically, the grasping portion and flange may be formed of two clam shell pieces 712, 714 configured as a housing 715 with an exterior wall 715.5 that defines an open interior 717. The clam shell pieces when assembled capture within an annular recess 716 a rear flange 718 at a rear end 719 of a nose piece 720, also part of the housing 715. An O-ring 726 in an O-ring groove 728 of the nose piece 720 may provide for sealing of the housing as well as an improved tightness and firmness in the connection 729 between the nose piece and the two clam shell pieces. Thus, the nose piece 720 and the two clam shell 712, 714 pieces are exteriorly exposed components of the housing. The fiber optic line 732 extends through the open interior 717 and through an internal component of the body portion configured as a rigid bushing 733. The bushing 733 is captured between the rear end 719 of the nose piece and the two clam shell pieces by way of stop portions 734, 735 configured as a wall portions unitary with the clam shell pieces. The wall portions 734, 735 and nose piece 720 defining a slot 740 for receiving and seating of the bushing. The rigid bushing 733 is radially centered and has a central aperture 742 for the fiber optic line 732 and a forward facing central bushing recess 743 defined by the bushing annular wall 744 for receiving an elastomeric member configured as a resilient and compliant bushing or block 745. The bushing may have a rearward extension 733.2 that may be used to position an RFID tag 745.6 within the housing. In embodiments, the housing components and rigid bushing may be formed from injection molded polymers.

Figure 4:
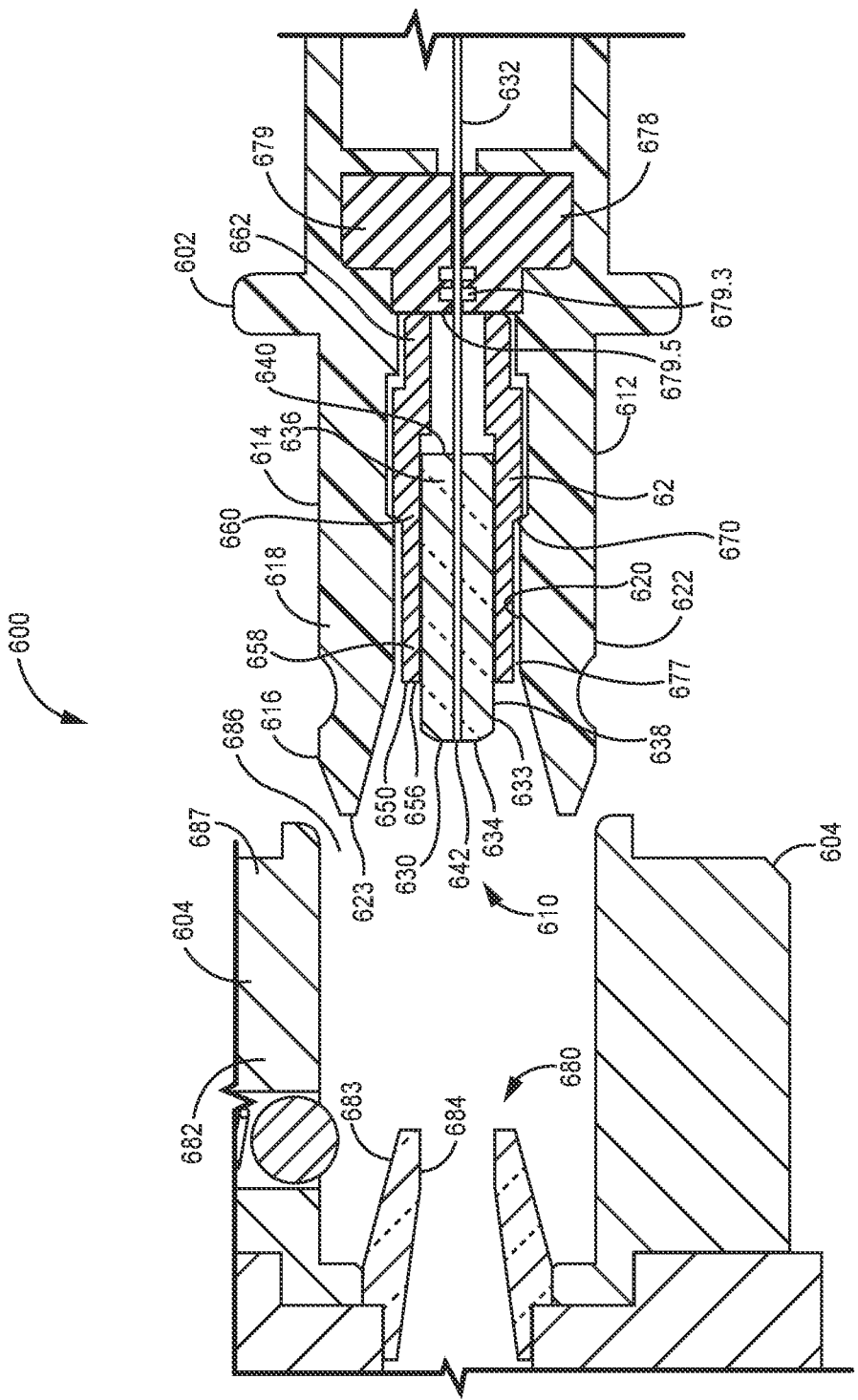
FIG. 4 is a cross sectional view of the coupling of FIG. 3 in an uncoupled state.
Figure 5:
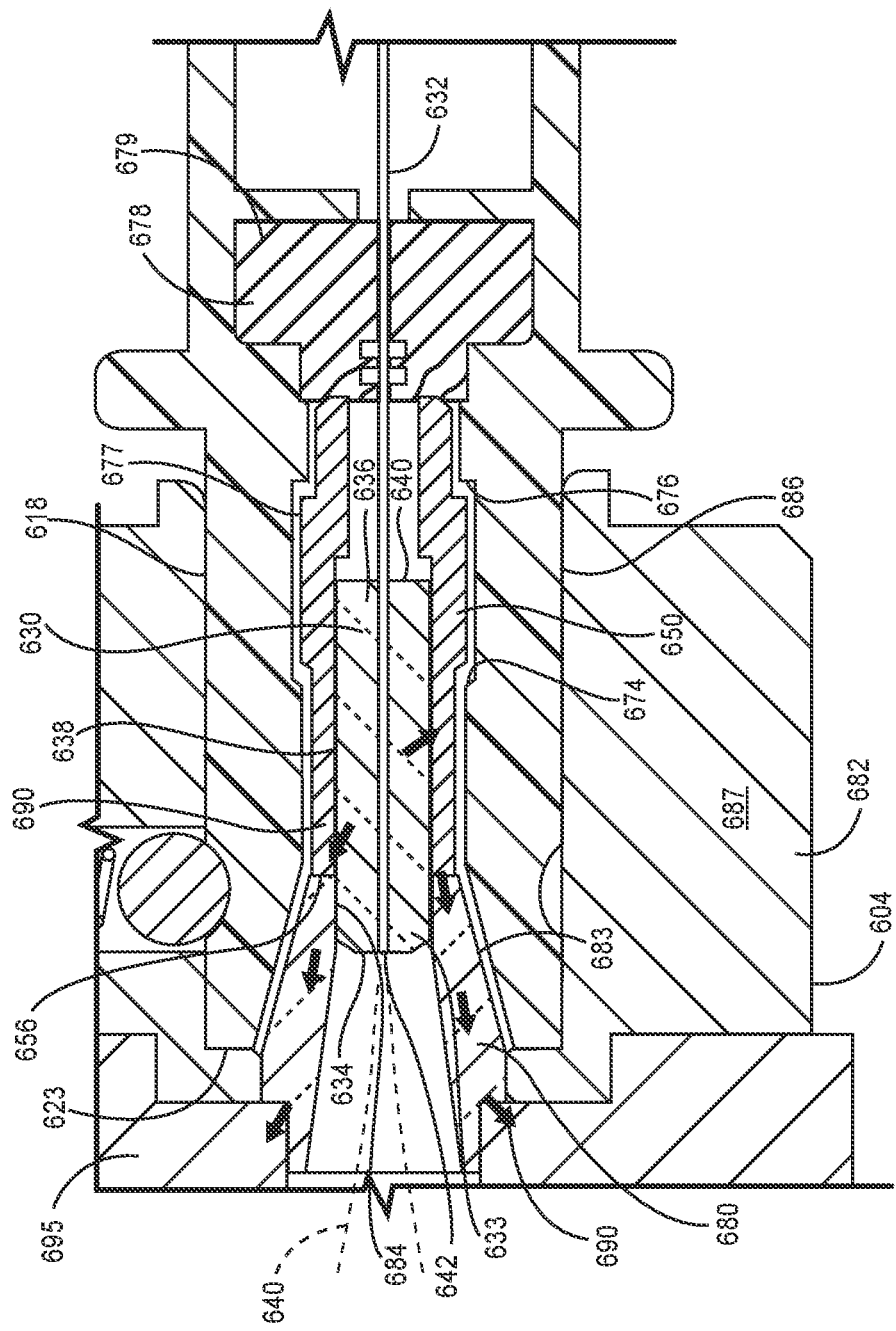
FIG. 5 is an enlarged detail of the cross section of FIG. 3.
Figure 6:
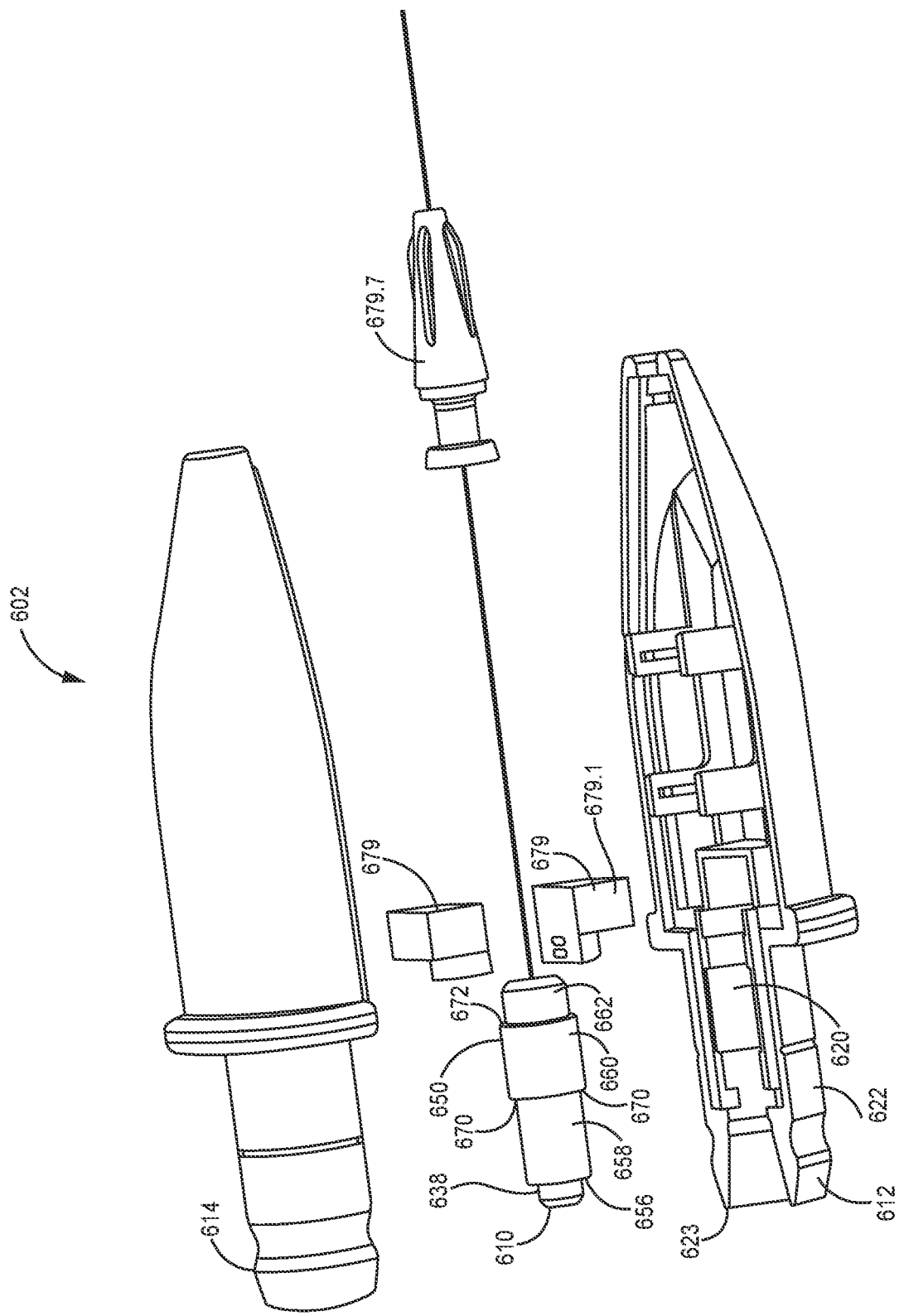
FIG. 6 is an exploded view of the launch connector of FIG. 3.
Figure 7:
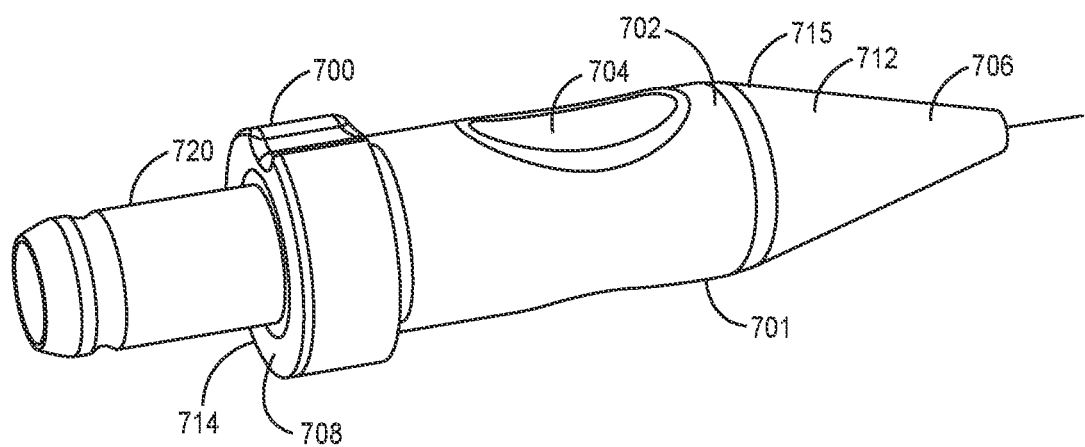
FIG. 7 is a perspective view of another embodiment of a launch connector.

Referring to FIG. 10, the fiber optic line extends into male ferrule 711 and has an exposed facet 750 at the forward end 752 of the ferrule. The male ferrule may be formed of stainless steel or other materials. The forward end may have a recess known as a power well 753 such that laser radiation that overfills the forward facet of the fiber will be out of focus when it hits the ferrule. The forward end has a lead-in tapered portion 754 with an exterior surface 755 and a first forward cylindrical portion 758 with a cylindrical exterior surface 759 of a first radius r1. Another second forward cylindrical portion 764 with a cylindrical exterior surface 765 and a second radius r2 extends rearward from the first forward cylindrical portion, and a mid or third cylindrical portion 768 with a cylindrical exterior surface 767 and a third radius r3, is rearward of the second forward cylindrical portion. A rearward cylindrical portion 770 with a cylindrical exterior surface 771 adjoins the third cylindrical portion and rearward or fourth radius r4. In embodiments, the second radius r2 is greater than the first radius r1, the third radius r3 is greater than the second radius r2 and is also greater than the fourth radius r4. In embodiments, the fourth radius r4 may equal the second radius r2. The mid or third cylindrical portion 768 defines a intermediate cylindrical band 776 with a forward stop surface 777 and a rearward stop surface 778. The ferrule is constrained axially and radially within the ferrule cavity 780 defined by the interior wall surface 782 of the nose piece and the interior surface 783 of the bushing 733. The ferrule cavity has a conforming fit to the shape of the ferrule. Interior shoulder 785 on the nose piece wall provide axial stops for constraining the male ferrule. The inward facing cylindrical surfaces 782 of the nose piece defining the ferrule cavity provide radial or lateral stop surfaces. The male ferrule is configured substantially like the male ferrule and rigid sleeve of the embodiment of FIGS. 3-6, except the male ferrule is unitary is and entirely formed of stainless steel or other material. This embodiment of the launch connector 602 will also interface with a laser energy generator connector and the female ferrule such as illustrated in FIGS. 3 and 4. The heat management may be enhanced of the embodiment of FIGS. 3 and 4 in that the entirety of the ferrule is stainless steel which may facilitate better heat conductance and transfer. The cooperating female ferrule may also be stainless steel providing significant regions of metal to metal contact between the respective optical connection portions of the launch connector and the laser energy generator connector.

Continuing to refer to FIG. 10, in embodiments, the first radius may be 0.055 to 0.070 inches. The second radius may be 0.090 to 0.110 inches, and the third radius may be 0.110 to 0.125 inches, and the fourth radius may be 0.090 to 0.110 inches. In embodiments, the difference in radius measurement between the second and third radii is from 0.015 inches to 0.020 inches. In embodiments, the difference in radius measurement between the fourth and third radii is from 0.015 inches to 0.020 inches. In embodiments, when the ferrule or ferrule in a fitting is centrated in the form fit cavity of the body portion, there is a minimal gap between the outer surface of the ferrule or ferrule in a fitting of 0.005 to 0.020 inches all around the ferrule or ferrule in a fitting measured in a radial direction.

The fiber optic line may be conventionally secured with epoxy 788 or the like within the rear recess of the male ferrule. The elastomeric block 745 may have two portions 745.1, 745.2 configured as halves as shown in FIGS. 8 and 9 that clamp about the fiber optic line. An axial groove 790 may be in one or both portions. In embodiments the groove is undersized with respect to the fiber optic line. Additionally, the elastomeric portions may be slightly oversized with respect to the bushing recess such that when the two elastomeric block halves are sandwiched around the fiber optic line and inserted into the bushing recess, there is an interference fit with respect to the fiber optic line and the block halves, as well with respect to the block halves and the bushing, such that the block halves are compressed and clamp about the fiber optic line thereby clamping the fiber optic line holding it in place. Due to the flexible resilience of the elastomeric block material the engagement still allows some forward and rearward movement of the fiber optic line 732 with respect to the housing, such movement would be mostly in an axial direction. A central circumferential recess 745.8 about the elastomeric block may enhance the forward-rearward freedom of movement of the fiber optic line when it is clamped in the block, that is, increasing compliancy. As such the block acts as an elastomeric clamp on the fiber optic line. Additionally, as the block halves are sandwiched around the fiber optic line, the optical connection portion, comprising the male ferrule or a male ferrule seated in a rigid sleeve fitting, may be pulled to the forward facing surface of the elastomeric block to contact or slightly depress the elastomeric block at the blocks forward face. This provides a centration to the optical connection portion with the rearward portion of the ferrule or fitting engagement with the face being radially spaced and distributed about the fiber optic line's forward exit point of the elastomeric block. In embodiments, the forward face may be conforming shaped to the rearward end of the ferrule or fitting. In embodiments, the optic fiber line may be in slight tension between optical connection portion and the elastomeric block thereby pulling the optical connection portion into and deflecting the elastomeric block, providing a more firm centration of the optical connection portion.

Referring to FIGS. 11-13B, an additional embodiment of a launch connector 800 is illustrated with a housing 801 with a grasping portion 804, a forward flange 808, and a plug portion or forward nose portion 810 extending forward from the forward flange for plugging into a laser energy generator such as is illustrated in FIGS. 1-5. A tail portion configured as a strain relief member 811 secures the fiber optic cable 812.

Figure 12:
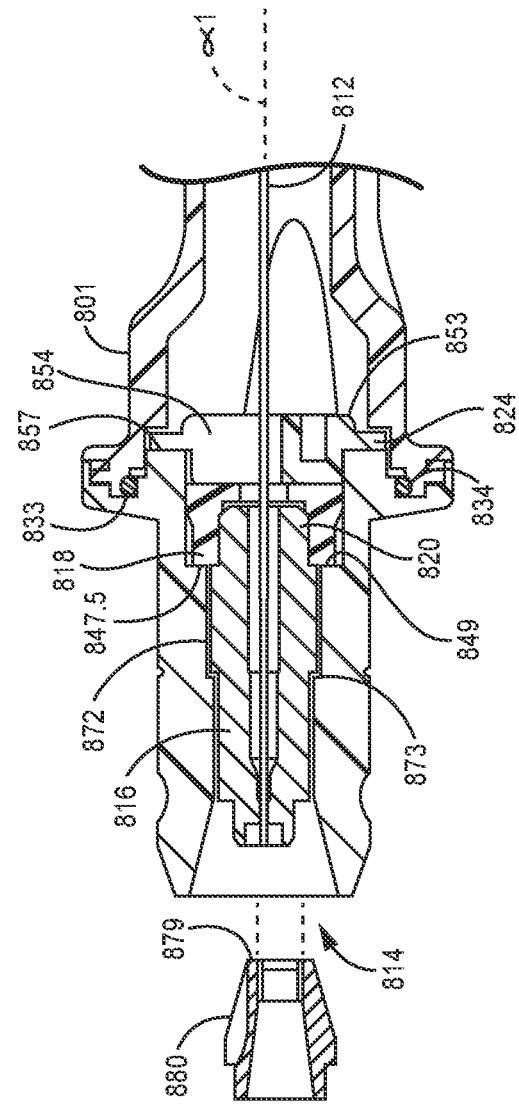
FIG. 12 is a cross sectional view of the launch connector of FIG. 11 along with a female ferrule that receives the male ferrule of the launch connector.
Figure 13A:
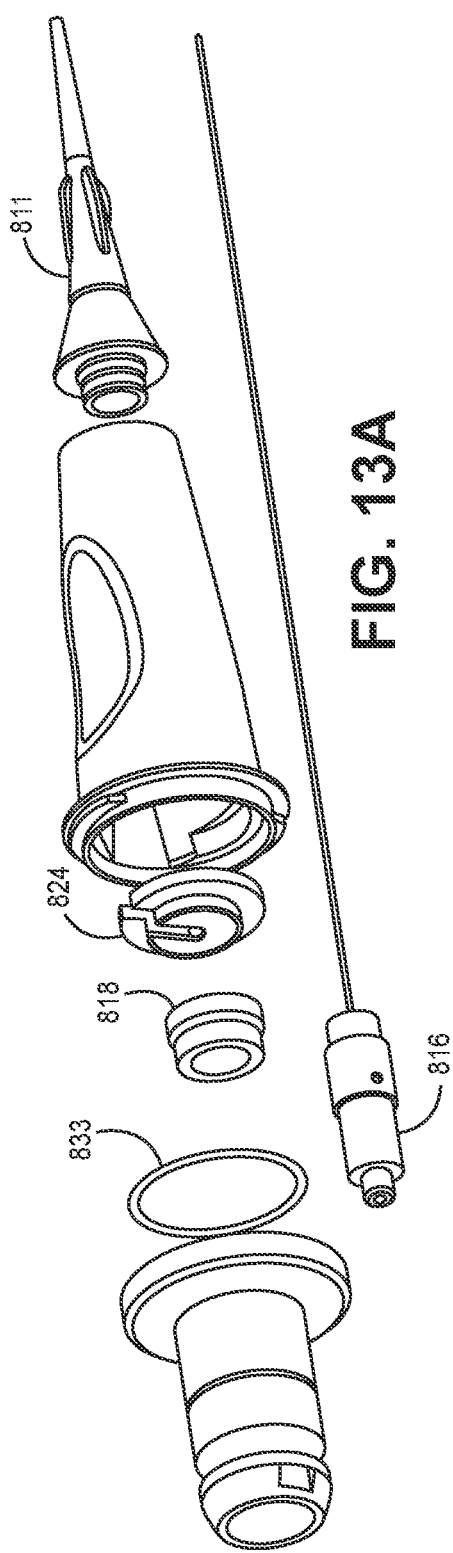
FIG. 13A is an exploded view of the launch connector of FIG. 11.
Figure 13B:
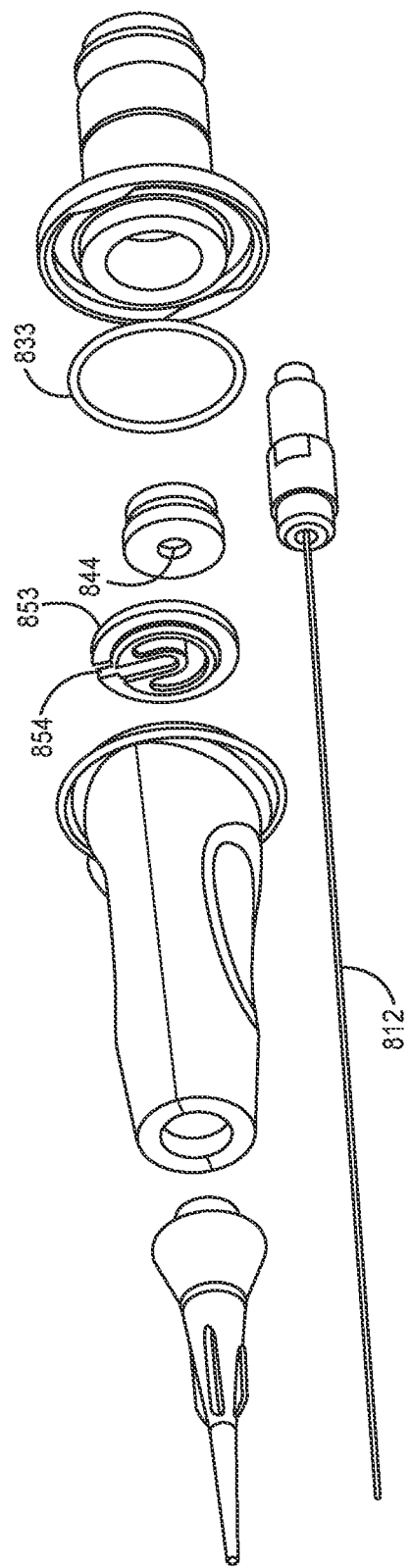
FIG. 13B is an exploded view of the launch connector of FIG. 11.
Figure 14A:
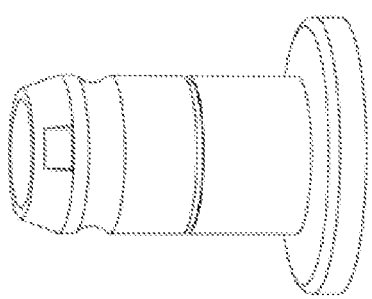
FIGS. 14A and 14B are perspective views of the forward nose portion of the connector of FIG. 11.
Figure 15A:
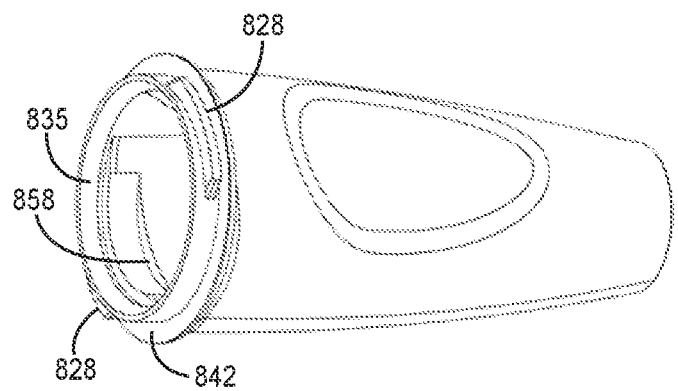
FIGS. 15A and 15B are perspective views of the body portion or housing of the launch connector of FIG. 11.
Figure 14B:
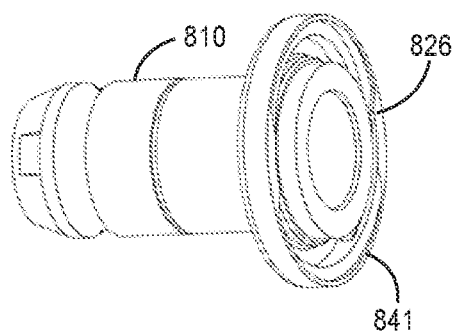
Figure 15B:
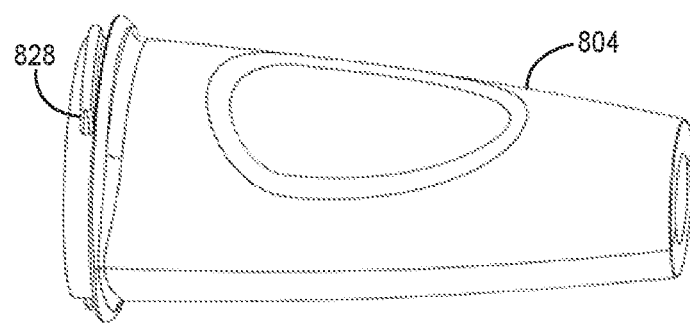
Figure 14C:
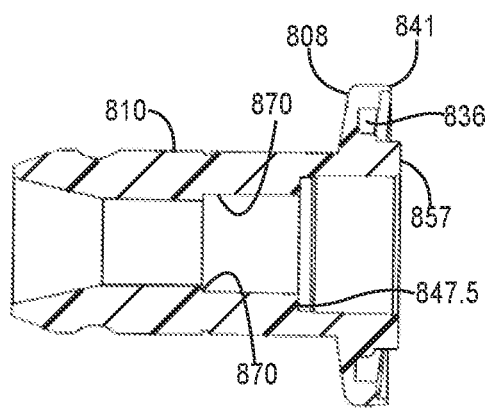
FIG. 14C is a cross sectional view of the nose portion of FIGS. 14A and 14B.
Figure 15C:
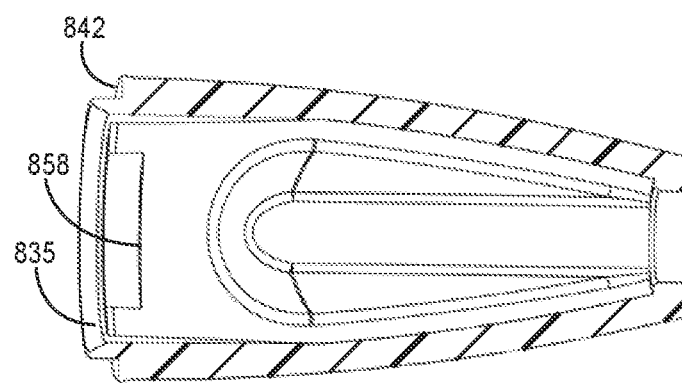
FIG. 15C is a cross sectional view of the housing of FIGS. 15A and 15B.
Figure 17A:
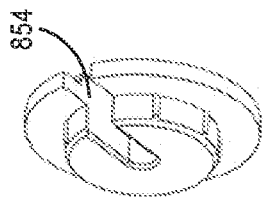
FIGS. 17A and 17B are perspective views of a block of elastomeric material configured as a bushing and functioning as an elastomeric support.
Figure 18A:
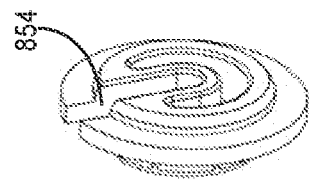
FIGS. 18A and 18B are perspective views of a retainer for the elastomeric support of FIG. 17C.
Figure 18C:
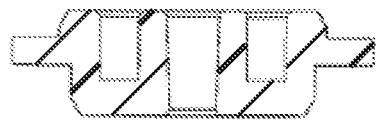
FIG. 18C is a cross sectional view of the retainer of FIGS. 18A and 18B.
Figure 17B:
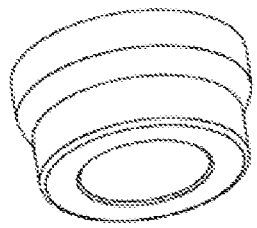
Figure 18B:
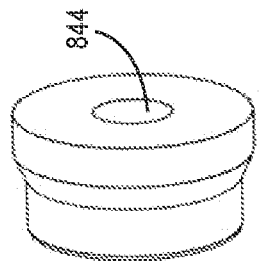
Figure 17C:
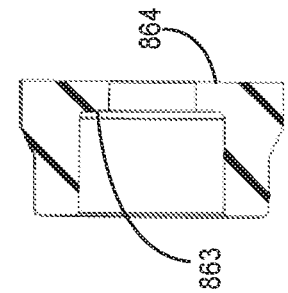
FIG. 17C is a cross sectional view of the elastomeric support of FIGS. 17A and 17B.

Referring to FIGS. 12-13D, the connector 800 generally comprises a mechanical connection portion 813 formed of the housing, particularly the plug portion 810 and forward flange 808, and also comprises an optical connection portion 814 formed of the male ferrule 816, an elastomeric support 818 that captures a rearward end 820 of the male ferrule 816, and a retainer 824 for securing the elastomeric support with respect to the housing 801. The components of the housing 801 that are assembled are the nose portion 810 and the grasping portion 804, each of which have cooperating rotational attachment portions 826, 828 that are illustrated as having threads 830 allowing joinder of the components with a partial rotation. An O-ring 833 may be positioned in the juncture 834 between the plug portion 810 and the grasping portion. The grasping portion may have an O-ring engaging surface 835 that is oblique to the axis α1 of the launch connector. The O-ring seats in an annular groove 836 of the flange portion 838 of the nose portion 810. Such an angled surface allows full locking rotation of the cooperating threaded components such that distally positioned annular stop surfaces 841, 842 on the respective components abut one another, providing a tight juncture. Additionally, the O-ring provides an expansive or separation force between the engaged components at the juncture which is believed to effectively lock the components together such that they do not inadvertently come apart. The O-ring also provides a hermetic seal at the juncture 834.

The elastomeric support 818 may be configured as a cup shaped bushing with a central aperture 844 for the optic fiber 812 and a U shape in cross section as shown in FIG. 12, with the rearward end of the male ferrule seated in the recess. The support 818 seats in an annular recess 846 of the rearward end 847 of the nose portion 810 and a forwardmost and forward facing annular surface 847.5 of the forwardly extending annular wall 847.7 of the elastomeric support 818 abuts against a nose portion interior shoulder 848 with a rearward facing annular shoulder surface 849 that is perpendicular to the axis α1. The support may be compressed by the retainer 853 shaped as a disk with a radial slot 854 that facilitates assembly allowing the retainer to be slid over the optic fiber 812 during assembly. The retainer has a peripheral flange that seats and is sandwiched between respective annular engagement surfaces 857, 858 of the nose portion 810 and the grasping portion 804. Advantageously, the forwardmost and forward facing annular surface 847.5 of the elastomeric support also engages the male ferrule at the rearward shoulder 860 at rearward facing annular surface 861. This provides a "soft" resilient and compliant axial positioning of the male ferrule in the interior of the housing that is conformingly shaped to the male ferrule. Additionally, the inside bottom seating surface 863 of the base 864 of the elastomeric support may further engage the rearward facing rearwardmost surface of the male ferrule 816 providing further resilient and compliant axial positioning of the male ferrule.

Continuing to refer to FIGS. 11-18C, as in previous embodiments, the male ferrule may have a forward facing shoulder 867 with a forward facing annular face or surface 868. The forward facing shoulder 867 confronting a rearwardly facing interior shoulder 870 of the nose portion providing the conforming shape of the wall of the nose portion to the shape of the male ferrule with a circumferential gap 872 and an axial gap 873 at the forward facing shoulder of the male ferrule. As best shown in FIG. 12, the forward facing face 868 of the male ferrule cooperates with the annular face 879 of the female ferrule 880 providing a path for heat dissipation of the heat generated at the front end of the male ferrule when laser energy is focused thereon.

Figure 16A:
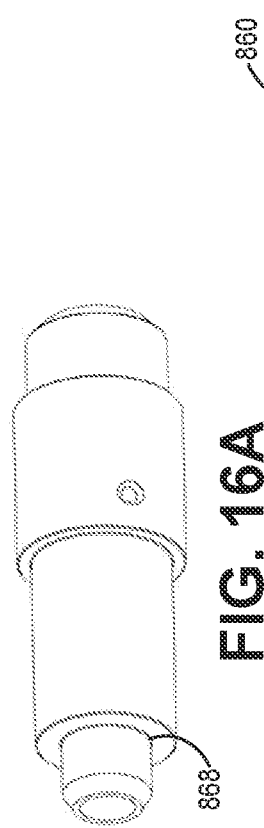
FIGS. 16A and 16B are perspective views of the male ferrule of the launch connector of FIG. 1.
Figure 16B:
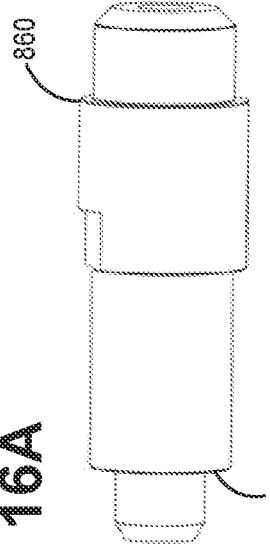
Figure 16C:
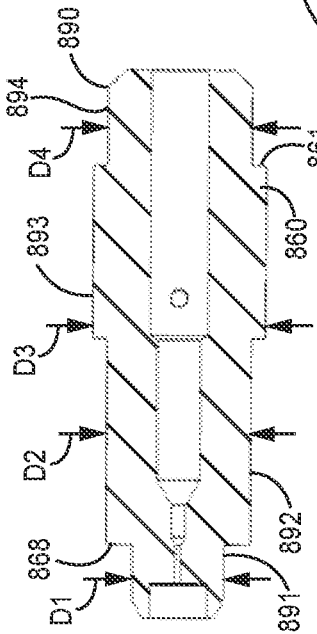
FIG. 16C is a cross sectional view of the male ferrule of FIGS. 16A and 16B.
Figure 16D:
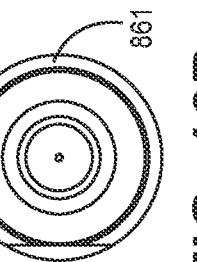
FIG. 16D is a forward end view of the male ferrule of FIG. 16A-16C.

Referring in particular to FIG. 16C, the optical connection component 890 is configured as a unitary male ferrule. A first or forward cylindrical portion 891 has a first diameter D1, a second or intermediate cylindrical portion 892 has a second diameter D2 greater that the first diameter. A third cylindrical portion which is also a second intermediate cylindrical portion 893 has a third diameter D3 which is greater than the first diameter and greater than the second diameter. A rearward or fourth cylindrical portion 894 has a rearward or fourth diameter D4 that is less than the diameter of the second intermediate cylindrical portion and greater than the diameter D1 of the forward cylindrical portion 891. In embodiments, the unitary optical connection component may comprise stainless steel.

In embodiments, the mechanical connection portions may be configured as bayonet connections, screw on connections, press fit connections, or detent connections. In embodiments, the elastomeric support may be replaced by other resilient compliant supports, for example, coil spring configurations may be suitable in some embodiments.

The following U.S. patents/publications are incorporated by reference for all purposes: U.S. Pat. Nos. 5,329,541; 5,337,386; 5,907,650; 5,943,460; 6,238,103; 7,503,701; 8,419,293; 8,888,378; 9,329,350; 9,393,081; 9,395,496; 9,429,713; 10,082,632; and US 2019/0094472.

The invention is not restricted to the details of the foregoing embodiment(s). The invention extends to any novel one, or any novel combination, of the features disclosed in this specification (including any incorporated by reference references, any accompanying claims, abstract and drawings), or to any novel one, or any novel combination, of the steps of any method or process so disclosed. The above references in all sections of this application are herein incorporated by references in their entirety for all purposes.

Although specific examples have been illustrated and described herein, it will be appreciated by those of ordinary skill in the art that any arrangement calculated to achieve the same purpose could be substituted for the specific examples shown. This application is intended to cover adaptations or variations of the present subject matter. Therefore, it is intended that the invention be defined by the attached claims and their legal equivalents, as well as the following illustrative aspects. The above described aspects embodiments of the invention are merely descriptive of its principles and are not to be considered limiting. Further modifications of the invention herein disclosed will occur to those skilled in the respective arts and all such modifications are deemed to be within the scope of the invention.

We claim:

1. An optical fiber connector coupling for connecting a laser radiation source to a device, the coupling comprising a launch connector having a forward end, a rearward end and an axis, the launch connector comprising a body portion with an optical fiber extending into the body portion at the rearward end, the launch connector having a mechanical connection portion defined by the body portion and an optical connection portion, the optical connection portion contained within the mechanical connection portion and comprising a male ferrule connected to the optical fiber, the optical fiber having a forwardly exposed facet at a forward end of the ferrule, a block of compliant elastomeric material centrally positioned within the body portion about the launch connector axis, the block configured as a cup with a central aperture, the cup receiving a rearward end of the optical connection portion, the cup positioned at a shoulder of the optical connection portion, and abutting a rearward facing surface of the optical connection portion.

2. The optical fiber connector coupling of claim 1, wherein the optical connection portion has a forward facing annular face displaced rearwardly from the forward most end of the male ferrule, the annular surface providing a stop surface for the optical connection portion when connecting the launch connector.

3. The laser light energy coupling of claim 1, wherein the body portion defines a housing with a cavity sized for providing a circumferential gap between the optical portion and the housing, thereby constraining the optical portion within the housing while allowing radial, forward and rearward movement of the optical connection portion.

4. The laser light energy coupling of claim 1, wherein the body portion has a forward nose piece with a tubular portion containing the optical connection portion, the forward nose piece having a cavity, the forward nose piece form fit to the optical connection portion but with a gap between the optical connection portion and the nose piece, whereby the optical connection portion has constrained movement in the cavity.

5. An optical fiber connector coupling for connecting a laser radiation source to a device, the coupling comprising a launch connector having a forward end, a rearward end and an axis, the launch connector comprising a body portion with an optical fiber extending into the body portion at the rearward end, the launch connector having a mechanical connection portion defined by the body portion and an optical connection portion, the optical connection portion contained within the mechanical connection portion and comprising a male ferrule connected to the optical fiber, the optical fiber having a forwardly exposed facet at a forward end of the ferrule, a block of compliant elastomeric material centrally positioned within the body portion about the launch connector axis and abutting a rearward facing surface of the optical connection portion, wherein the fiber optic line is clamped within the elastomeric block thereby providing axial compliancy to the fiber optic line.

6. An optical fiber connector coupling for connecting a laser radiation source to a device, the coupling comprising a launch connector having a forward end, a rearward end and an axis, the launch connector comprising a body portion with an optical fiber extending into the body portion at the rearward end, the launch connector having a mechanical connection portion defined by the body portion and an optical connection portion, the optical connection portion contained within the mechanical connection portion and comprising a male ferrule connected to the optical fiber, the optical fiber having a forwardly exposed facet at a forward end of the ferrule, a block of compliant elastomeric material centrally positioned within the body portion about the launch connector axis, the block configured as a cup with a central aperture, the cup receiving a rearward end of the optical connection portion and abutting a rearward facing surface of the optical connection portion wherein the body portion has a forward nose piece with a tubular portion containing the optical connection portion, the optical connection portion being generally cylindrical with a central circumferential band, the forward nose piece having a cavity form fit to the optical connection portion but with a gap between the optical connection portion and the nose piece whereby the optical connection piece has constrained movement therein.

7. An optical fiber connector coupling for connecting a laser radiation source to a device, the coupling comprising a launch connector having a forward end, a rearward end and an axis, the launch connector comprising a body portion with an optical fiber extending into the body portion at the rearward end, the launch connector having a mechanical connection portion defined by the body portion and an optical connection portion, the optical connection portion contained within the mechanical connection portion and comprising a male ferrule connected to the optical fiber, the optical fiber having a forwardly exposed facet at a forward end of the ferrule, a block of compliant elastomeric material centrally positioned within the body portion about the launch connector axis, the block configured as a cup with a central aperture, the cup receiving a rearward end of the optical connection portion and abutting a rearward facing surface of the optical connection portion, wherein the body portion has a forward nose piece with a tubular portion containing the optical connection portion, the body portion having a grasping portion rearward of the nose piece, the nose piece having a flange seated in an annular groove of the grasping portion, the connector coupling further comprising an O-ring positioned between the nose piece and the grasping portion.

* * * * *